United States Patent
Abedini et al.

(10) Patent No.: US 10,282,843 B2
(45) Date of Patent: May 7, 2019

(54) SYSTEM AND METHOD FOR LESION ANALYSIS AND RECOMMENDATION OF SCREENING CHECKPOINTS FOR REDUCED RISK OF SKIN CANCER

(71) Applicants: International Business Machines Corporation, Armonk, NY (US); MoleMap NZ Ltd., Auckland (NZ)

(72) Inventors: Mani Abedini, Pascoe Vale (AU); Adrian Bowling, Auckland (NZ); Rajib Chakravorty, Epping (AU); Sergey Demyanov, Melbourne (AU); Rahil Garnavi, Macleod (AU)

(73) Assignee: International Business Machines Corporation, Armonk, NY (US)

(*) Notice: Subject to any disclaimer, the term of this patent is extended or adjusted under 35 U.S.C. 154(b) by 245 days.

(21) Appl. No.: 15/336,347

(22) Filed: Oct. 27, 2016

(65) Prior Publication Data

US 2018/0122076 A1 May 3, 2018

(51) Int. Cl.
*G06K 9/00* (2006.01)
*G06T 7/00* (2017.01)
(Continued)

(52) U.S. Cl.
CPC ......... *G06T 7/0016* (2013.01); *A61B 5/0077* (2013.01); *A61B 5/444* (2013.01);
(Continued)

(58) Field of Classification Search
None
See application file for complete search history.

(56) References Cited

U.S. PATENT DOCUMENTS

| 6,075,879 A | 6/2000 | Roehrig et al. |
| 6,345,275 B2 | 2/2002 | Lee |

(Continued)

FOREIGN PATENT DOCUMENTS

WO 2005060466 A2 7/2005

OTHER PUBLICATIONS

Melanoma.org, "Melanoma Facts and Statistics," http://www.melanoma.org.au/understanding-melanoma/melanoma-facts-and-statistics/, 2016, 2 pages.

(Continued)

*Primary Examiner* — Sean M Conner
(74) *Attorney, Agent, or Firm* — David Quinn; Ryan, Mason & Lewis, LLP

(57) ABSTRACT

A method for image analysis comprises receiving one or more current images of a lesion from a body of a person, wherein the one or more current images are electronically captured by and transmitted from a capture device, and analyzing the one or more current images, wherein the analyzing comprises performing image processing to compare the one or more current images captured at a first time to one or more previous images of the lesion captured at a second time prior to the first time, and determining at least one difference between the one or more current images and the one or more previous images based on the comparing. The method further comprises determining a probability that the lesion will become diseased based on the analysis, and recommending a time for a future image capture of the lesion and/or a consultation with a practitioner based on the determined probability.

17 Claims, 6 Drawing Sheets

(51) Int. Cl.
*G06T 3/00* (2006.01)
*A61B 5/00* (2006.01)
*G16H 50/00* (2018.01)

(52) U.S. Cl.
CPC .......... *A61B 5/6898* (2013.01); *A61B 5/7267* (2013.01); *G06T 3/0068* (2013.01); *A61B 5/0002* (2013.01); *A61B 2576/02* (2013.01); *G06T 2207/10004* (2013.01); *G06T 2207/20076* (2013.01); *G06T 2207/20081* (2013.01); *G06T 2207/20084* (2013.01); *G06T 2207/30096* (2013.01); *G16H 50/00* (2018.01)

(56) References Cited

U.S. PATENT DOCUMENTS

| | | | |
|---|---|---|---|
| 6,993,167 | B1 | 1/2006 | Skladnev et al. |
| 7,415,143 | B2 | 8/2008 | Grichnik |
| 7,457,659 | B2 | 11/2008 | Maschke |
| 7,539,334 | B2 | 5/2009 | Corrion |
| 8,837,796 | B1 | 9/2014 | Zalutskaya |
| 9,089,303 | B2 | 7/2015 | Chen et al. |
| 9,092,697 | B2 | 7/2015 | Manson et al. |
| 2005/0228264 | A1* | 10/2005 | Grichnik .............. A61B 5/0059 600/411 |
| 2007/0053561 | A1 | 3/2007 | Corrion |
| 2007/0100226 | A1* | 5/2007 | Yankelevitz ......... A61B 5/1075 600/407 |
| 2007/0177786 | A1 | 8/2007 | Bartels |
| 2007/0208263 | A1* | 9/2007 | John .................... A61B 5/0452 600/509 |
| 2011/0123087 | A1 | 5/2011 | Nie et al. |
| 2011/0129129 | A1 | 6/2011 | Avinash et al. |
| 2011/0218428 | A1 | 9/2011 | Westmoreland et al. |
| 2011/0237938 | A1* | 9/2011 | Mizuno ................ G06T 7/0012 600/425 |
| 2011/0273535 | A1 | 11/2011 | Mendelson |
| 2012/0008838 | A1 | 1/2012 | Guyon et al. |
| 2014/0142413 | A1 | 5/2014 | Chang et al. |
| 2015/0205998 | A1 | 7/2015 | Suh et al. |
| 2015/0302270 | A1 | 10/2015 | BenHimane et al. |
| 2016/0157787 | A1 | 6/2016 | Merritt et al. |
| 2016/0364529 | A1* | 12/2016 | Li .......................... G06F 19/321 |
| 2017/0061621 | A1* | 3/2017 | Wortman ............... A61B 5/442 |
| 2017/0076451 | A1 | 3/2017 | Pauly |
| 2018/0075597 | A1* | 3/2018 | Zhou ....................... G06F 19/00 |
| 2018/0103932 | A1* | 4/2018 | Tahmasebi Maraghoosh ............. A61B 8/085 |

OTHER PUBLICATIONS

Skincancer.org, "Skin Cancer Facts & Statistics," http://www.skincancer.org/skin-cancer-information/skin-cancer-facts#treatment, Jun. 8, 2016, 6 pages.

A. Scope et al., "The 'Ugly Duckling' Sign: Agreement Between Observers," Journal of Archives of Dermatology, Jan. 2008, pp. 58-64, vol. 144, No. 1.

I. Maglogiannis et al., "Overview of Advanced Computer Vision Systems for Skin Lesions Characterization," IEEE Transactions on Information Technology in Biomedicine, Sep. 2009, pp. 721-733, vol. 13, No. 5.

L.W.C. Chan et al., "Machine Learning of Patient Similarity," IEEE International Conference on Bioinformatics and Biomedicine Workshops, 2010, pp. 467-470.

C.A. Morton et al., "Clinical Accuracy of the Diagnosis of Cutaneous Malignant Melanoma," British Journal of Dermatology, Feb. 1998, pp. 283-287, vol. 138, No. 2.

J.J. Grob et al., "The 'Ugly Duckling' Sign: Identification of the Common Characteristics of Nevi in an Individual as a Basis for Melanoma Screening," Journal of Archives of Dermatology, Jan. 1998, pp. 103-104, vol. 134, No. 1.

List of IBM Patents or Patent Applications Treated as Related.

* cited by examiner

401

402

SYSTEM AND METHOD FOR LESION ANALYSIS AND RECOMMENDATION OF SCREENING CHECKPOINTS FOR REDUCED RISK OF SKIN CANCER

BACKGROUND

Melanoma is one of the most common cancers in Australian and United States populations. In the United States, 76,380 new cases of invasive melanoma are estimated to be diagnosed in 2016. In 2016, it is estimated that 10,130 people will die of melanoma. The annual cost of treating melanoma is estimated as $3.3 billion. Therefore, besides being fatal, melanoma can affect multiple stages of a societal fabric.

While melanoma can be a fatal disease, it can be treated fully when detected early, by for example, an excisional biopsy. Typically, early detection of melanoma in a skin mole or other lesion is assessed by the presence/absence of certain features in the mole or other lesion. These examinations are usually formed as defined protocols used by health care professionals. There exist several such protocols such as, for example, "ABCD Rule", "Menzies Rule", "3 point checklist", etc. Common features across these different protocols can include the presence of certain "colors" (brown, black, red, etc.) and/or patterns (networks, globules, etc.). When examined under dermoscopy or other clinical imagery, health care professionals look for signatures and assign a score to the mole or other lesion. The decision to perform a biopsy occurs if the score exceeds a predefined threshold, the value of which may vary depending on rules and/or protocols.

In general, the first point of contact for assessing skin moles or other lesions are individuals in the general population (e.g., the patients or their family members), nurses or general practitioners, who are not experts or specialists in the field of dermatology or skin cancer. Early detection of melanoma can be very important, resulting, for example, in a 95% to 97% 5 to 10 year survival rate when skin cancer early detection takes place. However, assessing fatal or critical cancerous lesions can be a difficult exercise for the non-expert, and experts are not always readily available, especially in some remote areas. Moreover, individuals may not be aware of the benefits of early detection, and their appointments to see specialists about their skin may not be kept or scheduled too far apart.

SUMMARY

According to an exemplary embodiment of the present invention, a method for image analysis comprises receiving one or more current images of a lesion from a body of a person, wherein the one or more current images are electronically captured by and transmitted from a capture device, and analyzing the one or more current images of the lesion, wherein the analyzing comprises performing image processing to compare the one or more current images of the lesion captured at a first time to one or more previous images of the lesion captured at a second time prior to the first time, and determining at least one difference between the one or more current images and the one or more previous images of the lesion based on the comparing. The method further comprises determining a probability that the lesion will become diseased based on the analysis, and recommending at least one of a time for a future image capture of the lesion and a consultation with a practitioner based on the determined probability.

According to an exemplary embodiment of the present invention, a system for image analysis comprises a memory and at least one processor coupled to the memory, wherein the at least one processor is configured to receive one or more current images of a lesion from a body of a person, wherein the one or more current images are electronically captured by and transmitted from a capture device, and analyze the one or more current images of the lesion, wherein in analyzing, the at least one processor is further configured to perform image processing to compare the one or more current images of the lesion captured at a first time to one or more previous images of the lesion captured at a second time prior to the first time, and determine at least one difference between the one or more current images and the one or more previous images of the lesion based on the comparing. The at least one processor is also configured to determine a probability that the lesion will become diseased based on the analysis, and recommend at least one of a time for a future image capture of the lesion and a consultation with a practitioner based on the determined probability.

According to an exemplary embodiment of the present invention, a computer program product for image analysis comprises a computer readable storage medium having program instructions embodied therewith, the program instructions executable by a processor to cause the processor to perform a method comprising receiving one or more current images of a lesion from a body of a person, wherein the one or more current images are electronically captured by and transmitted from a capture device; and analyzing the one or more current images of the lesion, wherein the analyzing comprises performing image processing to compare the one or more current images of the lesion captured at a first time to one or more previous images of the lesion captured at a second time prior to the first time, and determining at least one difference between the one or more current images and the one or more previous images of the lesion based on the comparing. The method also comprises determining a probability that the lesion will become diseased based on the analysis, and recommending at least one of a time for a future image capture of the lesion and a consultation with a practitioner based on the determined probability.

These and other exemplary embodiments of the invention will be described or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which.

DETAILED DESCRIPTION

Figure 1:
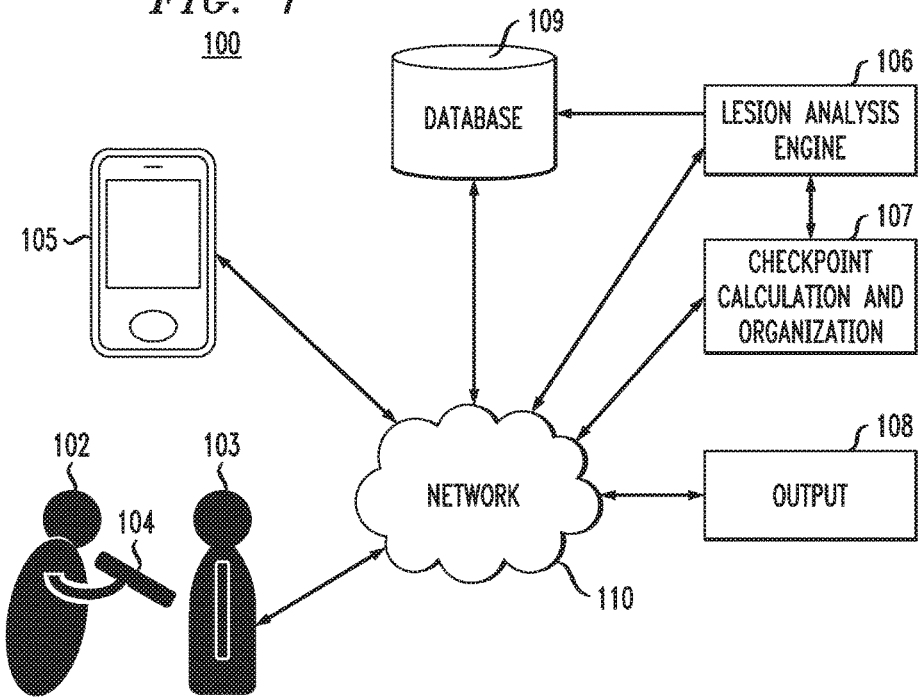
FIG. 1 is block diagram illustrating a system for lesion analysis and disease probability determination, according to an exemplary embodiment of the present invention.

Exemplary embodiments of the invention will now be discussed in further detail with regard to image analysis and, in particular, to using image analysis to perform temporal analysis of one or more lesions and determine disease probability of the one or more lesions. This invention may, however, be embodied in many different forms and should not be construed as limited to the embodiments set forth herein.

Embodiments of the present invention relate to systems and methods which utilize the increased imaging capabilities of mobile and other devices to permit non-experts to obtain high quality lesion images, and have the images analyzed for a determination of whether skin cancer is likely, and whether and when appointments with skin cancer experts and/or further screenings should be scheduled. The embodiments of the present invention facilitate access to skin lesion monitoring systems, and provide improved methods for determining when follow-up screenings of potentially cancerous lesions should be conducted. Embodiments of the present invention enable a sufficient frequency of screening for those patients who may have limited access to health care providers.

According to an embodiment of the present invention, a user is able to monitor suspicious lesions. For example, the system may automatically analyze lesion images and other current and historical patient information collected by user (e.g., patient or non-expert clinician) in order to suggest a new screening check point or advise to visit a dermatologist. More specifically, the system may obtain a lesion image, perform an initial analysis of the lesion image, suggest if the lesion requires immediate attention by a specialist, such as a dermatologist, or suggest a time frame for a subsequent capture and analysis of the lesion image at a screening checkpoint. Depending on an initial assessment and a projected rate of lesion growth and/or evolution, a system, in accordance with an embodiment of the present invention, predicts the next checkpoint where the lesion should most likely be reevaluated. A system, according to an embodiment of the present invention, also can suggest that a user send a captured image to a dermatologist for further evaluation. The system can be configured to determine a frequency of screening checkpoints, and link a user to a domain expert under certain circumstances, such as when an emergency case is concluded or the system is not able to assess the severity of a lesion with a high degree of confidence (e.g., level of confidence not exceeding a threshold).

According to an embodiment, the system can also determine when to acquire an expert opinion for updating a diagnostic engine in order to improve the accuracy of the predictions and determinations made by the system.

As used herein, the term "real-time" refers to output within strict time constraints. Real-time output can be understood to be instantaneous or on the order of milliseconds or microseconds. Of course, it should be understood that depending on the particular temporal nature of the system in which an embodiment of the invention is implemented, other appropriate timescales that provide approximately contemporaneous performance and output can be achieved.

FIG. 1 is block diagram illustrating a system for lesion analysis and disease probability determination, according to an exemplary embodiment of the present invention. As shown in FIG. 1 by lines and/or arrows, the components of the system 100 are operatively connected to each other via, for example, physical connections, such as wired and/or direct electrical contact connections, and/or wireless connections, such as, for example, WiFi, BLUETOOTH, IEEE 802.11, and/or networks, including but not limited to, a local area network (LAN), wide area network (WAN), cellular network, ad hoc networks, WANET, satellite network or the Internet. For example, a network 110 can operatively link components 104, 105, 106, 107, 108 and 109 of the system 100.

By way of non-limiting example, in accordance with an embodiment of the present invention, referring to FIG. 1, the system includes a capture device 104 that is used by, for example, a practitioner 102, such as a doctor, nurse, physician's assistant, technician, etc., to capture images of any lesions and/or groups of lesions from a patient 103. The capture device 104 can include, but is not necessarily limited to, a camera, such as a still picture or video camera, scanner, specialized imaging device, tablet, and/or smart mobile device, such as a smart phone or tablet that can, for example, perform a full body or partial body scan of a patient 103. Similarly, the system 100 includes a capture device 105 that is used by, for example, a user (such as patient 103) and/or a friend or family member of the user to capture images of any lesions and/or groups of lesions from the user. The capture device 105 can include, but is not necessarily limited to, a camera, such as a still picture or video camera, scanner, specialized imaging device, tablet, and/or smart mobile device, such as a smart phone or tablet that can, for example, take a picture or perform a full body or partial body scan of the user. The capture devices 104, 105 can be further used to receive meta data inputs and/or sense meta data, the meta data including, for example, patient information, history, age, skin tone, and/or location on the body of respective lesions or groups of lesions. The capture devices 104, 105 can be configured to communicate wirelessly with each other and with the other components 106-109 of the system 100 over the network 110.

The database 109 can be used to store the meta data and images of lesions and/or groups of lesions that have been taken from a user (e.g., patient 103) in the past. The images stored in the database 109 can include, for example, images of the same lesion taken in the past, images of other lesions of the same patient, and images of lesions taken with different devices. The lesion images produced in accordance with embodiments of the present invention include, but are not necessarily limited to, dermoscopy, sonography, confocal microscopy, multiphoton tomography, or optical coherence tomography images.

The database 109 can be, for example, cloud-based. The data and images from the database 109 are electronically accessible by a lesion analysis engine 106 and checkpoint calculation and organization engine 107, for example, via the network 110 or directly, and are used by the lesion analysis engine 106 and checkpoint calculation and organization engine 107 when recommending a follow-up screening checkpoint or a consultation with a specialist (e.g., dermatologist). The database 109 is also configured to receive images and meta data from the capture devices 104 and 105, or other sources of patient images and data, via network 110 or directly.

The system 100 further includes the lesion analysis engine 106, which evaluates lesion images to determine a probability that lesion(s) which are the subject of the images are cancerous or will become cancerous. The lesion analysis engine 106 also recommends an immediate consultation with a specialist if it finds a high probability (e.g., above a certain threshold) that the lesion(s) are cancerous or will become cancerous. The results of the analysis by the lesion analysis engine 106 are received by the checkpoint calculation and organization engine 107, which determines and schedules a future screening point if the lesion analysis engine 106 does not find a need for an immediate consultation with a specialist. If the lesion analysis engine 106 does find a need for an immediate consultation with a specialist, a patient is notified, for example, in real-time via a communication network, of the need to schedule an appointment with a specialist, and the specialist also receives the image and the results of the analysis for review via the communication network. The receipt of the image and the results of the analysis for review can also be in real-time. In the case of a determination of a need for immediate consultation with a specialist, the checkpoint calculation and organization engine 107 can schedule an appointment for the patient with the specialist by, for example, accessing electronic calendars of the patient and specialist to determine mutual availability, or provide an emergent request (e.g., in real-time) to the patient and/or practitioner via a communication network to schedule an appointment.

The lesion analysis engine 106 and checkpoint calculation and organization engine 107 communicate with and transmit information to one or more output devices 108 either directly or via a network 110 so that a specialist, the patient 103, a non-expert practitioner 102 or other users with access to the system, can view the determinations made by the lesion analysis engine 106 and/or checkpoint calculation and organization engine 107 and decide on which actions to take for a patient 103. The output device 108 can include, for example, a desktop or portable computer, tablet, personal digital assistant (PDA), smart phone or other computing device having an interface for viewing the results, determinations or requests. According to an embodiment, the results, determinations or requests can be transmitted to the capture devices 104, 105, which can also function as an output device. The lesion analysis engine 106 also transmits analysis results and/or newly acquired images and data to the database 109, so that the database 109 can electronically store, and the lesion analysis engine 106 can electronically access these results and/or data from the database 109 when performing subsequent analyses as explained in more detail herein. The lesion analysis engine 106 and checkpoint calculation and organization engine 107 are explained in further detail herein in connection with FIGS. 2 and 3.

Figure 2:
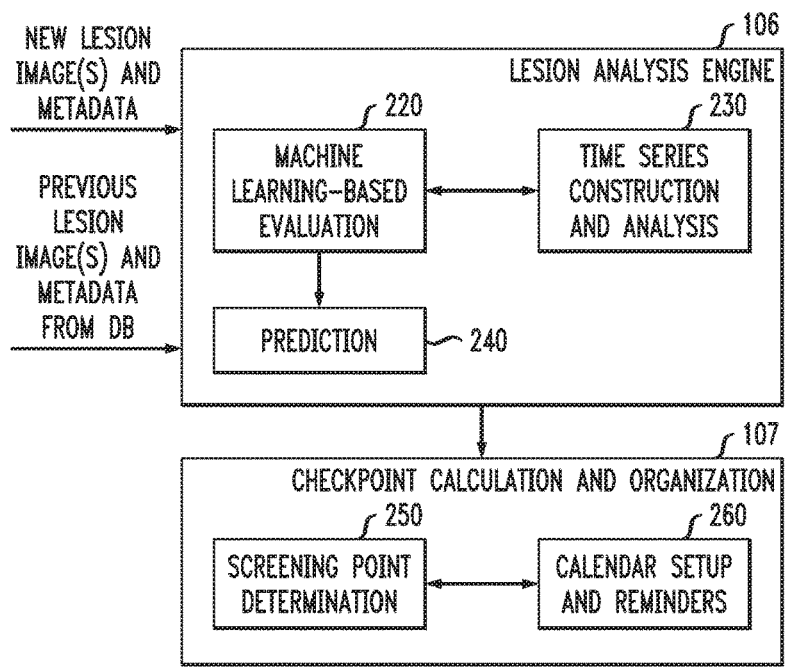
FIG. 2 is a block diagram illustrating a lesion analysis engine and a checkpoint calculation and organization engine in a system for lesion analysis and disease probability determination, according to an exemplary embodiment of the present invention.

FIG. 2 is a block diagram illustrating a lesion analysis engine 106 and a checkpoint calculation and organization engine 107, according to an exemplary embodiment of the present invention. Referring to FIG. 2, the lesion analysis engine 106 includes a machine learning-based evaluation module 220, a time series construction and analysis module 230, and a prediction module 240. According to an embodiment of the present invention, the lesion analysis engine 106 receives newly acquired imaging data and meta data of a user (e.g., patient 103) and previously acquired imaging data and meta data of the user, which can be transmitted to the lesion analysis engine 106 from the capture device 104 or 105 and/or the database 109, for example, via network 110.

The newly acquired imaging data includes, for example, current images of one or more lesions from a patient's body that have been captured and are to be analyzed by the lesion analysis engine 106 in view of past images of the one or more lesions that were taken at an earlier time (such as, for example, months or years previous). The lesion analysis engine 106 performs a temporal analysis of current images in view of previous images to determine an evolution and/or growth of a lesion(s), and whether the lesion(s) is progressing to cancer or some other disease.

To the extent that meta data, for example, age, family history, and/or behavior (e.g., wearing sunscreen, exposure to sunlight, eating and exercise habits) may change over time, these factors and any variances are taken into consideration by the lesion analysis engine 106 when determining a probability of cancer in a patient. The considered meta data of a patient can include, but is not necessarily limited to, data about the images, such as location on the body, and factors that may be relevant when assessing a risk of cancer, such as, age, gender, race, geographic location, behavior, family history, etc.

Figure 3:
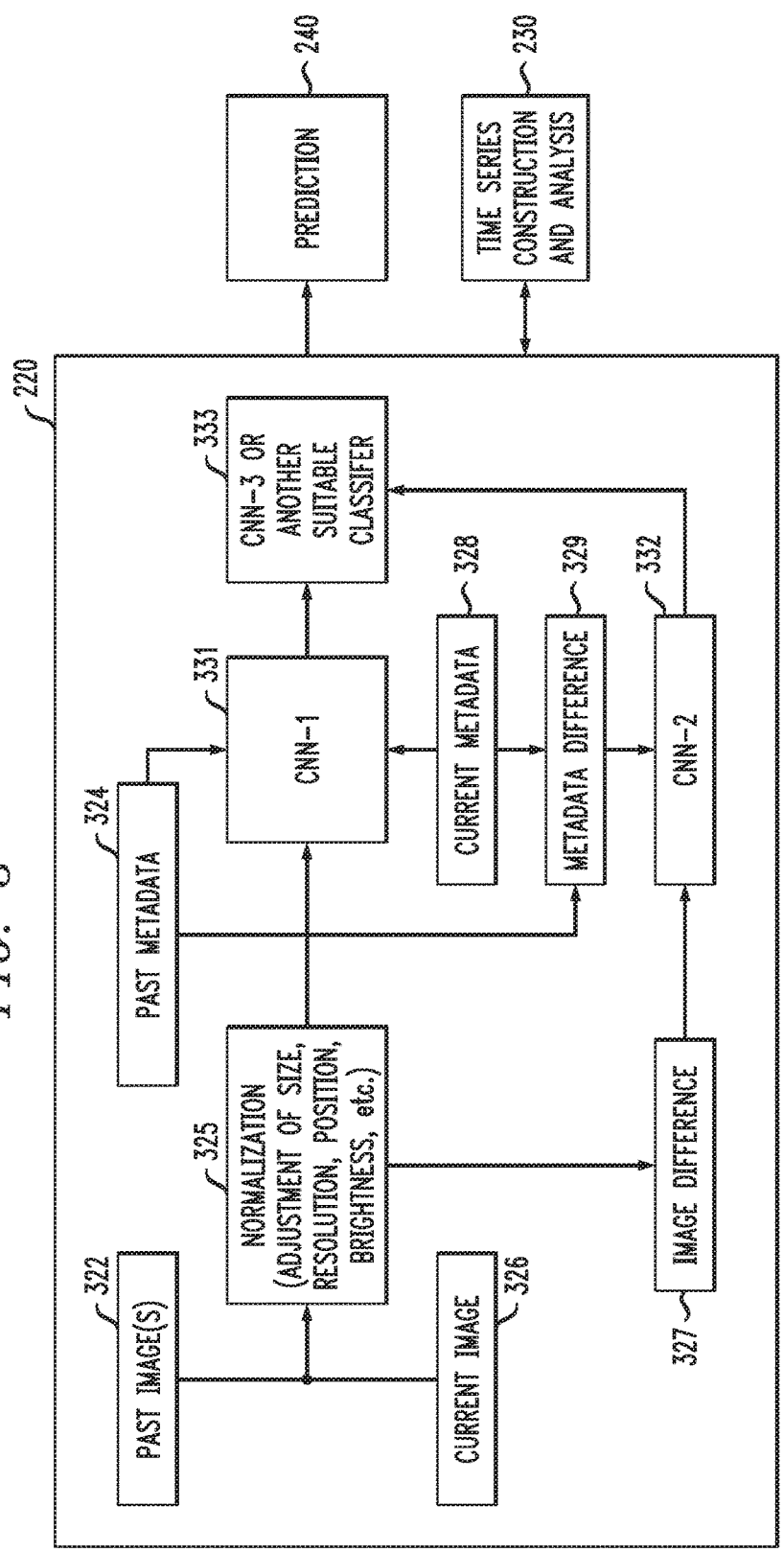
FIG. 3 is a block diagram illustrating a convolutional neural network evaluation module, a time series construction and analysis module, and a prediction module in a system for lesion analysis and disease probability determination, according to an exemplary embodiment of the present invention.

Referring to FIG. 3, the machine learning-based evaluation module 220 includes one or more machine learning-based engines, such as, for example, convolutional neural network (CNN) engines CNN-1 (331), CNN-2 (332) and CNN-3 (333), which evaluate the current and past images of a patient's lesions, and metadata differences when determining whether lesions are or will become cancerous. In accordance with an embodiment of the present invention, a time sequence of lesion images can be used to electronically generate an approximation of lesion appearance at any point in time between a time the first (earliest) image was taken and the last (latest) image was taken. The approximation is used to obtain pairs of images with a fixed time interval between them (e.g., 1 month).

Other machine learning based engines which can be used as an alternative to CNNs include, for example, visual analytic models which receive an image, perform visual feature extraction and feature learning, build prediction models and assess (e.g., classify) input image disease status (e.g., cancerous or non-cancerous) along with a confidence factor.

As used herein, a "convolutional neural network (CNN)" can refer to a feed-forward artificial neural network used in machine learning in which the connectivity pattern between its neurons are arranged in such a way that they can mathematically be described by a convolution operation.

Pairs of consecutive images with a fixed time interval between them are processed by a machine learning based engine, such as CNN, but not necessarily limited to a CNN. In accordance with an embodiment of the present invention, the images are preprocessed by a normalization component 325 to digitally transform the data structures of the images to result in images having the same size, resolution, brightness, etc., and which are linearly aligned to each other, such that the outcome removes the variations in conditions of an image capturing process, such as, for example, camera position and light strength.

According to an embodiment of the present invention, CNN-1 (331) is used to process an arithmetical difference between images at different times (e.g., between current images 326 and past images 322, and between pairs of multiple past images 322). The arithmetical difference is calculated by subtracting the prediction of CNN-1 for a current image from the prediction of CNN-1 for a previous image. CNN-1 evaluates the likelihood of suspicious cases for given images, so the difference of evaluation over time presents the progression of disease (e.g., cancer) for the same lesion. CNN-1 determines the arithmetical difference in view of past metadata 324, and current metadata 328. CNN-1 receives both image and meta data for a point in time and determines a diagnosis. As a result, both meta data and the image of a specific time in the past (or present) are complementary information for CNN-1 to predict a likelihood of a lesion being diseased (e.g., cancer).

CNN-2 (332) processes qualitative differences 327 between images at different times, such as, for example, differences in size of lesions, shape (e.g., contour) of lesions, symmetry/asymmetry of the lesions, nature of boundaries at edges of the lesions (e.g., abrupt, gradual), and/or color of the lesion (e.g., brown, black, yellow or gray). In accordance with a non-limiting embodiment of the present invention, the lesion analysis engine 106 is configured to detect qualitative differences 327, such as in size, shape, symmetry/asymmetry, nature of boundaries and color which are not detectable or discernable by the human eye. CNN-2 further takes into consideration qualitative differences 329 between metadata at different times (e.g., between current metadata 328 and past metadata 324, and between pairs of multiple instances of past metadata 324), such as, for example, changes in family history, at-risk behavior, age, etc.

CNN-3 (333) processes the outputs of CNN-1 and CNN-2 to yield a combined result, which is transmitted to the prediction module 240, which outputs the probability of a lesion to be one or more of a predefined set of diseases, or none of the predefined set of diseases.

Using a statistical model, such as, but not necessarily limited to, a Hidden Markov Model (HMM), the time series construction and analysis module 230 analyzes a time series of scores for probabilities of lesions being a disease. Other statistical and time series modeling methods can include, but are not necessarily limited to, neural networks, recurrent neural networks (RNNs), and autoregressive integrated moving average (ARIMA) models.

The outputs of the CNNs 331, 332 and 333 for pairs of consecutive images are considered as an observed variable for a statistical model (e.g., HMM) with the states corresponding to a predefined set of diseases, and none of the diseases. The statistical model considers not only the previous image, but also all other images taken in the past. The automated outputs of CNNs are predicted labels (e.g., cancerous, non-cancerous) with confidence values, or a probability of belonging to a label.

The machine learning based engines (e.g., CNN-1, CNN-2 and CNN-3) are trained to visually assess new images using sequences of lesion images with known diagnosis. This supervised training is based on images that have been labeled as diseased or not diseased by specialists. Each of the machine learning based engines (e.g., CNN-1, CNN-2 and CNN-3) are trained with different images from each other, so that the training strategies vary between the machine learning based engines.

In accordance with an embodiment of the present invention, the trained variables are the parameters of CNN-1, CNN-2 and CNN-3, which are the transition and output probabilities of the statistical model (e.g., HMM). CNN-1, CNN-2 and CNN-3 are trained using a label for a new image, and the architectures of CNN-1, CNN-2 and CNN-3 are defined using performance on a validation set. The statistical model (e.g., HMM) is trained using the diagnoses for each time point as hidden variables. The MINI will automatically learn the transition of a lesion from a benign state to a diseased (e.g., cancerous) state by observing the training samples. This transition is presented as a time series of diagnosis predictions and associated confidence values (e.g., CNN output probabilities).

In accordance with an embodiment of the present invention, using the machine learning based analysis engines 331, 332 and 333, the lesion analysis engine 106 performs an assessment for a mole or other lesion, and computes a safe interval when the lesion is likely to remain benign, or recommends to visit a dermatologist if the lesion is likely to be malignant. Based on the analysis by the lesion analysis engine 106, if the lesion is determined not likely to be malignant, the checkpoint calculation and organization engine 107, and more particularly, the screening point determination component 250 determines a safe time to wait for the next screening point where another image of the lesion should be captured and analyzed. The calendar setup and reminders component 260 electronically accesses a user's calendar, for example, on their mobile device or other device, checks for an open date and/or time, and automatically inputs a new calendar entry for the next screening checkpoint at an available date, along with periodic reminders of the next screening date. The checkpoint calculation and organization engine 107 can also periodically send electronic reminders via a communication network to a user prior to, as well as on the day of the next screening point. In addition, should the lesion analysis engine 106 determine that a user consult a specialist (e.g., dermatologist), the calendar setup and reminders component 260 can electronically access both a patient's and the specialist's calendars and availabilities, and suggest the closest mutually available appointment dates to the specialist and the patient.

In accordance with an embodiment of the present invention, the checkpoint calculation and organization engine 107 uses the statistical model (e.g., HMM) transition probabilities to identify the point in time when the probability of a lesion becoming malignant exceeds a predefined threshold. This point in time can be suggested as the next screening date. The checkpoint calculation and organization engine 107 can also be configured to provide a time frame for a next screening check point, where upper and lower limits for the time to the next screening can be defined according to different confidence thresholds for determining a probability of a lesion becoming malignant. The different confidence thresholds are discussed further herein in connection with FIGS. 4A and 4B. The checkpoint calculation and organization engine 107 can also be configured to set multiple reminders and set frequencies of reminding based on the proximity of a particular point in time to the upper limit.

The system 100 can also be configured to utilize different reminding techniques including, but not limited to, calendar reminders, text message (e.g. short message service (SMS)) reminders, email reminders or phone calls. The reminding technique used may depend on the initial assessment and/or severity of the patient's condition, and the proximity of the next checkpoint.

Figure 4A:
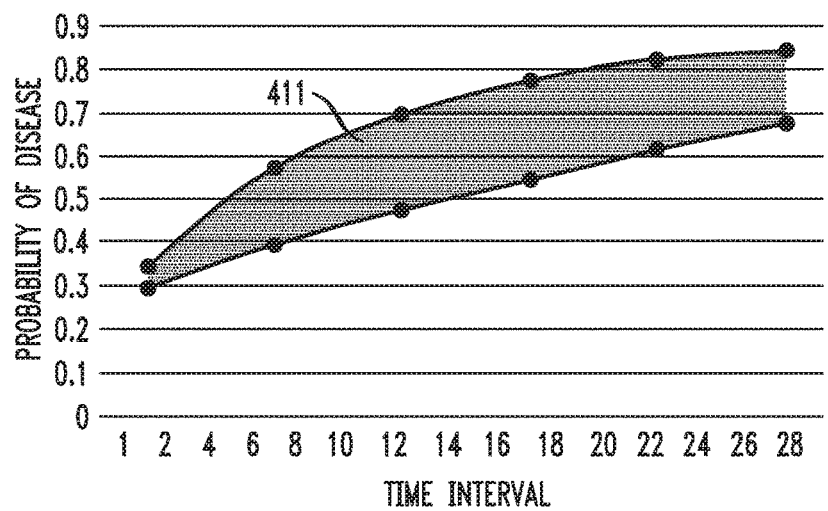
FIGS. 4A and 4B are plots illustrating prediction time series representing pessimistic and optimistic progression of a lesion towards becoming cancer, according to an exemplary embodiment of the present invention.
Figure 4B:
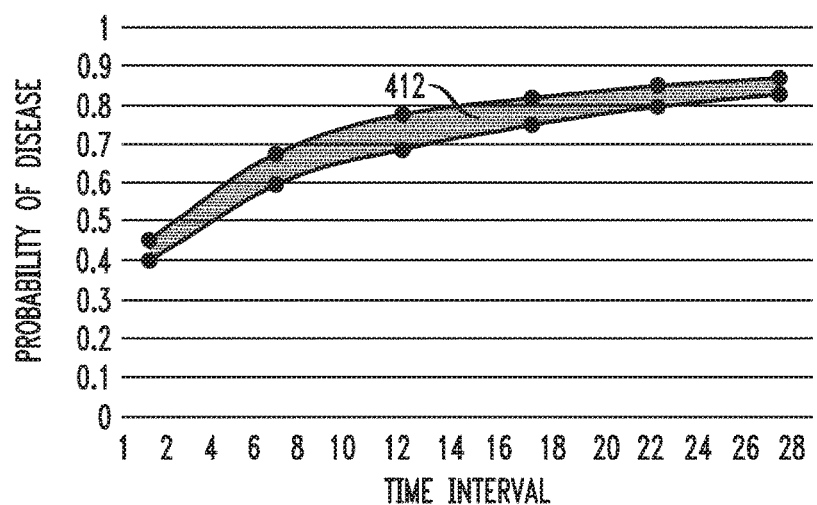

FIGS. 4A and 4B are plots illustrating prediction time series representing pessimistic and optimistic progression of a lesion towards becoming cancer. According to an exemplary embodiment of the present invention, the lesion analysis engine 106 can calculate the probability of a lesion becoming cancerous over a time interval (e.g., years, months, days), and produce two prediction time series; one based on high confidence and the other based on low confidence. These models can be based on different features or the same features and are tuned with different confidence thresholds. In connection with the same or different features, the models can have similar topology (e.g., input feature set) or a different topology.

Referring to FIGS. 4A and 4B, the upper lines of plots 401 and 402 illustrate pessimistic (low confidence threshold) progressions indicating a higher probability of disease at each time interval, while the lower lines of plots 401 and 402 illustrate optimistic (high confidence threshold) progressions indicating a lower probability of disease at each time interval. For example, at about time interval 18 (e.g., 18 months), the pessimistic curve of plot 401 indicates an approximately 80% chance of disease, while the optimistic curve of plot 401 indicates an approximately 50% chance of disease. At about time interval 16 (e.g., 16 months), the pessimistic curve of plot 402 indicates an approximately 82% chance of disease, while the optimistic curve of plot 402 indicates an approximately 75% chance of disease.

The gaps 411, 412 between the two trends (pessimistic and optimistic) in both plots 401 and 402 represents possible error in the system prediction. As can be seen from a comparison of plots 401 and 402, as more lesion images are captured over time and given to the system to provide more images to analyze in plot 402, the system produces more confident predictions and the gap 412 between the trends narrows when compared with the gap 411 for plot 401. The plot 401 is based on less data, so that predictions are not as accurate as in plot 402.

According to an embodiment of the present invention, if the system 100 is not able to conclude whether a lesion is or will become cancerous, the system sends the lesion image, for example, via a communication network, to one or more specialists (e.g., dermatologists) to clarify a diagnosis. The system compares the results of the specialists' determinations with the results of the system's analysis of the lesion image, and uses the obtained diagnosis from the one or more specialists for further system training of one or more of the machine learning based analysis engines.

Even if the system 100 is able to conclude whether a lesion is or will become cancerous, the system can still send the lesion image to one or more specialists in order to validate the reliability of the system. In the event that there is disagreement between the specialist's determination and the system prediction, or between determinations of two or more specialists, or if a specialist is not confident about a particular diagnosis, a consensus decision based, for example, on votes by multiple specialists and the system's conclusions can be implemented to result in more accurate predictions, which can be used in training to incrementally improve the accuracy of the system's determinations.

The system 100 is configured to dynamically update and retrain as needed while in use, using diagnoses for cases when a user visits a specialist or when an image is sent for a remote evaluation. The machine learning based analysis engines (e.g., CNN-1, CNN-2 and CNN-3) can be trained to visually assess new images using sequences of lesion images corresponding to the diagnoses from the cases when the user visits a specialist or when an image is sent for a remote evaluation.

In accordance with an embodiment of the present invention, a user can manually send an image to a dermatologist at any time regardless of whether the system determines that consultation with a specialist is needed. If the system is configured to determine pricing for a user/subscriber and an assessment by a specialist is not recommended by the system, the system can be configured to charge the user a higher price if the user sends an image to a dermatologist for evaluation.

In a non-limiting illustrative example of the operation of a system 100 in accordance with an embodiment of the present invention, an individual is concerned about a lesion appearing on his/her skin, a recent increase in size and/or a change in properties (e.g., color, shape, etc.) in the lesion. The individual is not convinced that it is necessary to visit a general practitioner or a specialist, or perhaps there is no easy access to primary health services where the individual is located. The individual takes an image of the lesion using, for example, a capture device 105, and transmits the image via network 110 to the lesion analysis engine 106.

Using the components and modules described herein, lesion analysis engine 106 performs an analysis and predicts that the lesion is not presently cancerous, but determines that the lesion may potentially evolve to become cancerous. The checkpoint calculation and organization engine 107 outputs a recommendation that the individual screen the lesion again in 6 months. The screening includes acquisition of additional images of the lesion and other relevant data, such as, for example, lifestyle changes (e.g., a significant period of time spent in sunlight, etc.)

In 6 months, the checkpoint calculation and organization engine 107 transmits an electronic reminder to a user device to take the next image, and the user captures a new image of the same lesion. The lesion analysis engine 106 performs another analysis and again returns the result as not presently cancer. The lesion analysis engine 106 also calculates size and pattern changes of the lesion in the last six months based on previous images stored in the database 109.

The lesion analysis engine 106 analyzes the changes, and identifies the changes as trending toward cancer. Using this output from the lesion analysis engine 106, the checkpoint calculation and organization engine 107 recommends the next checkpoint to be in 4 months, transmits this recommendation to the user, and sets a reminder.

In 4 months, the user captures another image of the lesion, and supplies other relevant information such as, for example, lifestyle changes or changed family history, to the lesion analysis engine 106. The lesion analysis engine 106 confirms that the changes to the lesion are still trending toward cancer, and the lesion is highly likely to be of the malignant type. The user is informed via a user device of these determinations by the lesion analysis engine 106, and the system sends the current image and previous lesion images if necessary to a dermatologist for further analysis (assuming permission by the patient to send the image(s) to a dermatologist has been obtained and granted). The image(s) and other data (e.g., patient history) is sent to the dermatologist, who confirms that there is a potential concern for melanoma. The checkpoint calculation and organization engine 107 receives the dermatologist's report and transmits a recommendation to the user that the user to make an appointment with a dermatologist for further careful examination, or automatically makes an appointment for the user as described herein. Results of analysis, and scheduling of screening checkpoints by system components can be performed in real-time upon capture and transmission of lesion images to the lesion analysis engine 106.

Figure 5:
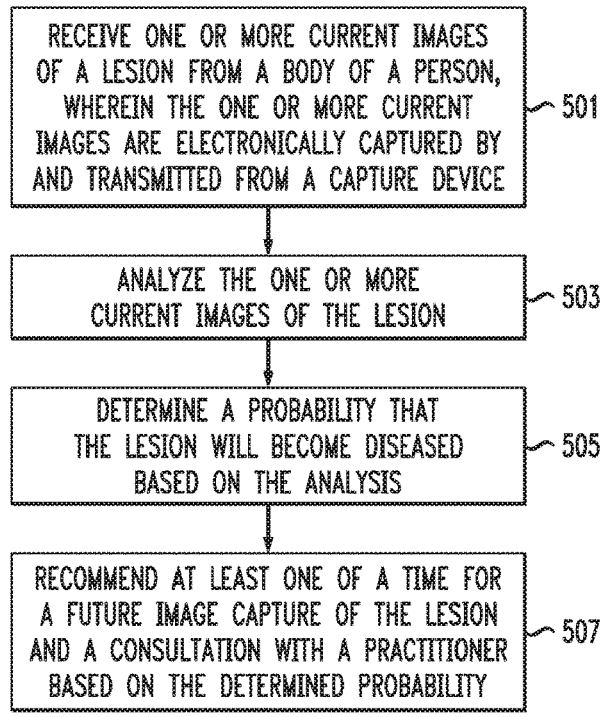
FIG. 5 is a flow diagram of a process for lesion analysis and disease probability determination, according to an exemplary embodiment of the invention.

FIG. 5 is a flow diagram of a process for lesion analysis and disease probability determination, according to an exemplary embodiment of the invention. Referring to FIG. 5, the process 500 includes, at block 501, receiving one or more current images of a lesion from a body of a person, wherein the one or more current images are electronically captured by and transmitted from a capture device. For example, as noted in connection with FIG. 1, a capture device 104 or 105 can capture an image of a lesion from different parts of the body of a user (e.g. patient 103), and transmit the captured images via, for example, a network 110, to a lesion analysis engine 106 where the images are received.

The process further includes, at block 503, analyzing the one or more current images of the lesion. The analyzing comprises performing image processing to compare the one or more current images of the lesion captured at a first time to one or more previous images of the lesion captured at a second time prior to the first time. In accordance with a non-limiting embodiment of the present invention, the comparison can be to determine differences in features in lesion images, such as, for example, changes in size, shape, symmetry/asymmetry, nature of boundaries and colors which may not be detectable or discernable by the human eye. In addition, an approximation of the appearance of the lesion at any point in time between the first time and the second time can be electronically generated. For example, image processing is performed to automatically morph (e.g., digitally transform a data structure) a first lesion image into a second lesion image.

According to an embodiment, the comparing is performed using at least one machine learning-based engine, such as, for example, a convolutional neural network (CNN), support vector machine (SVM), random forest, multi-layer perceptron, etc., which can be trained using lesion images each having a known label. The comparing can be performed using a plurality of machine learning based engines (e.g., CNN-1, CNN-2 and CNN-3), wherein each of the plurality of machine learning based engines is trained with a different set of lesion images from each other, each lesion image having a known label.

An output of a CNN for a pair of consecutive lesion images can be considered as an observed variable for a statistical model. In other words, a CNN can receive two consecutive images of a lesion as inputs (e.g., at time 1 and time 2), and predict if the lesion progressed from benign to a diseased (e.g., cancerous) state or not, which is the observed variable in a HMM model.

Performing the image processing can include preprocessing the one or more current images and the one or more previous images of the lesion to digitally transform the data structures of the images to result in images having at least one of a same size, a same resolution and a same brightness, and to be linearly aligned to each other.

The analyzing further comprises determining at least one difference between the one or more current images and the one or more previous images of the lesion based on the comparing. For example, in accordance with an embodiment of the present invention, a CNN determines arithmetical differences, while another CNN determines qualitative differences between the one or more current images and the one or more previous images of the lesion.

The process 500 further includes, at block 505, determining a probability that the lesion will become diseased based on the analysis, which can include building a time series of scores for probabilities that the lesion will become diseased, and analyzing the time series of scores using a statistical model.

At block 507, based on the determined probability, a time for a future image capture of the lesion and/or a consultation with a practitioner is recommended. The one or more current images can be automatically transmitted to a device of a specialist if the probability that the lesion will become diseased exceeds a threshold.

According to an embodiment of the present invention, recommending a time for future image capture of the lesion comprises identifying a time when the probability that the lesion will become diseased exceeds a predefined threshold, and assigning the identified time as the time for the future image capture of the lesion. Recommending a time for future image capture of the lesion may also include defining upper and lower limits for the future image capture of the lesion according to different confidence thresholds for determining the probability that the lesion will become diseased. For example, the prediction algorithm can be tuned to generate relatively low confidence, but a relatively narrower time frame in which the lesion will become concerning (e.g., perhaps developing to a diseased state), or predict a relatively wider time frame with relatively higher confidence, and anything in between. In principle, there is an inverse association between confidence level and size of a predicted time frame. A user can tune or the system can automatically tune parameters to control levels of confidence and control accuracy of a time frame.

In accordance with an embodiment of the present invention, metadata of the person can be analyzed, wherein the analyzing of the metadata comprises comparing current metadata corresponding to a later time to previous metadata corresponding to an earlier time than the later time, and determining at least one difference between the current metadata and the previous metadata based on the comparing. Determining of the probability that the lesion will become diseased is further based on the analysis of the metadata.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 6:
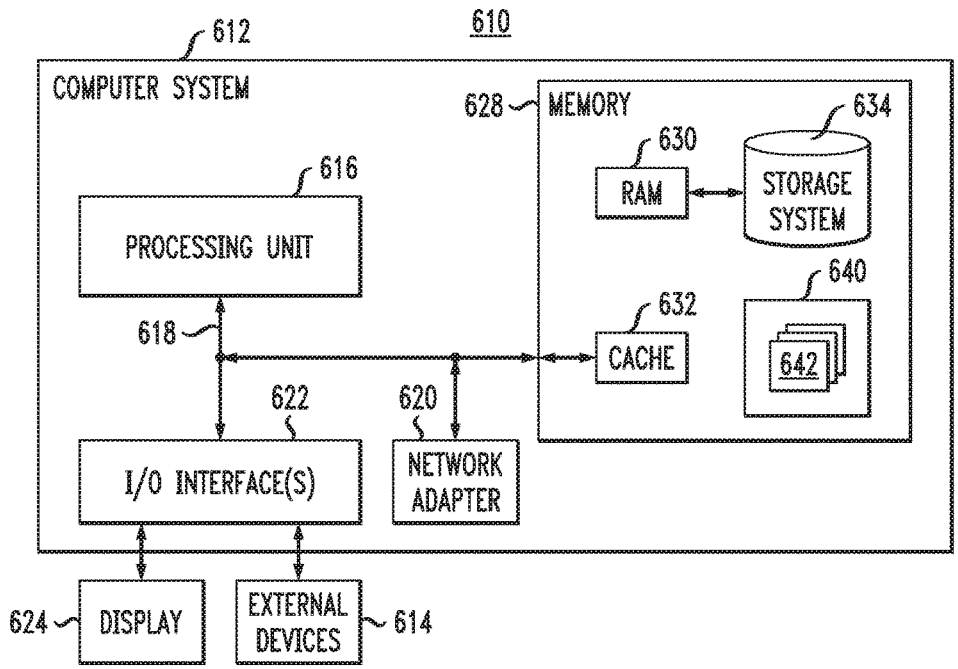
FIG. 6 illustrates a computer system in accordance with which one or more components/steps of the techniques of the invention may be implemented, according to an exemplary embodiment of the invention.

One or more embodiments can make use of software running on a general-purpose computer or workstation. With reference to FIG. 6, in a computing node 610 there is a computer system/server 612, which is operational with numerous other general purpose or special purpose computing system environments or configurations. Examples of well-known computing systems, environments, and/or configurations that may be suitable for use with computer system/server 612 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 612 may be described in the general context of computer system executable instructions, such as program modules, being executed by a computer system. Generally, program modules may include routines, programs, objects, components, logic, data structures, and so on that perform particular tasks or implement particular abstract data types. Computer system/server 612 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 612 in computing node 610 is shown in the form of a general-purpose computing device. The components of computer system/server 612 may include, but are not limited to, one or more processors or processing units 616, a system memory 628, and a bus 618 that couples various system components including system memory 628 to processor 616.

The bus 618 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 612 typically includes a variety of computer system readable media. Such media may be any available media that is accessible by computer system/server 612, and it includes both volatile and non-volatile media, removable and non-removable media.

The system memory 628 can include computer system readable media in the form of volatile memory, such as random access memory (RAM) 630 and/or cache memory 632. The computer system/server 612 may further include other removable/non-removable, volatile/nonvolatile computer system storage media. By way of example only, storage system 634 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 618 by one or more data media interfaces. As depicted and described herein, the memory 628 may include at least one program product having a set (e.g., at least one) of program modules that are configured to carry out the functions of embodiments of the invention. A program/utility 640, having a set (at least one) of program modules 642, may be stored in memory 628 by way of example, and not limitation, as well as an operating system, one or more application programs, other program modules, and program data. Each of the operating system, one or more application programs, other program modules, and program data or some combination thereof, may include an implementation of a networking environment. Program modules 642 generally carry out the functions and/or methodologies of embodiments of the invention as described herein.

Computer system/server 612 may also communicate with one or more external devices 614 such as a keyboard, a pointing device, a display 624, etc., one or more devices that enable a user to interact with computer system/server 612, and/or any devices (e.g., network card, modem, etc.) that enable computer system/server 612 to communicate with one or more other computing devices. Such communication can occur via Input/Output (I/O) interfaces 622. Still yet, computer system/server 612 can communicate with one or more networks such as a local area network (LAN), a general wide area network (WAN), and/or a public network (e.g., the Internet) via network adapter 620. As depicted, network adapter 620 communicates with the other components of computer system/server 612 via bus 618. It should be understood that although not shown, other hardware and/or software components could be used in conjunction with computer system/server 612. Examples, include, but are not limited to: microcode, device drivers, redundant processing units, external disk drive arrays, RAID systems, tape drives, and data archival storage systems, etc.

It is understood in advance that although this disclosure includes a detailed description on cloud computing below, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Computing node 610 in FIG. 6 can be an example of a cloud computing node. Computing node 610 is only one example of a suitable cloud computing node and is not intended to suggest any limitation as to the scope of use or functionality of embodiments of the invention described herein. Regardless, computing node 610 is capable of being implemented and/or performing any of the functionality set forth hereinabove. It is also to be understood that computing node 610 is not necessarily a cloud computing node.

Figure 7:
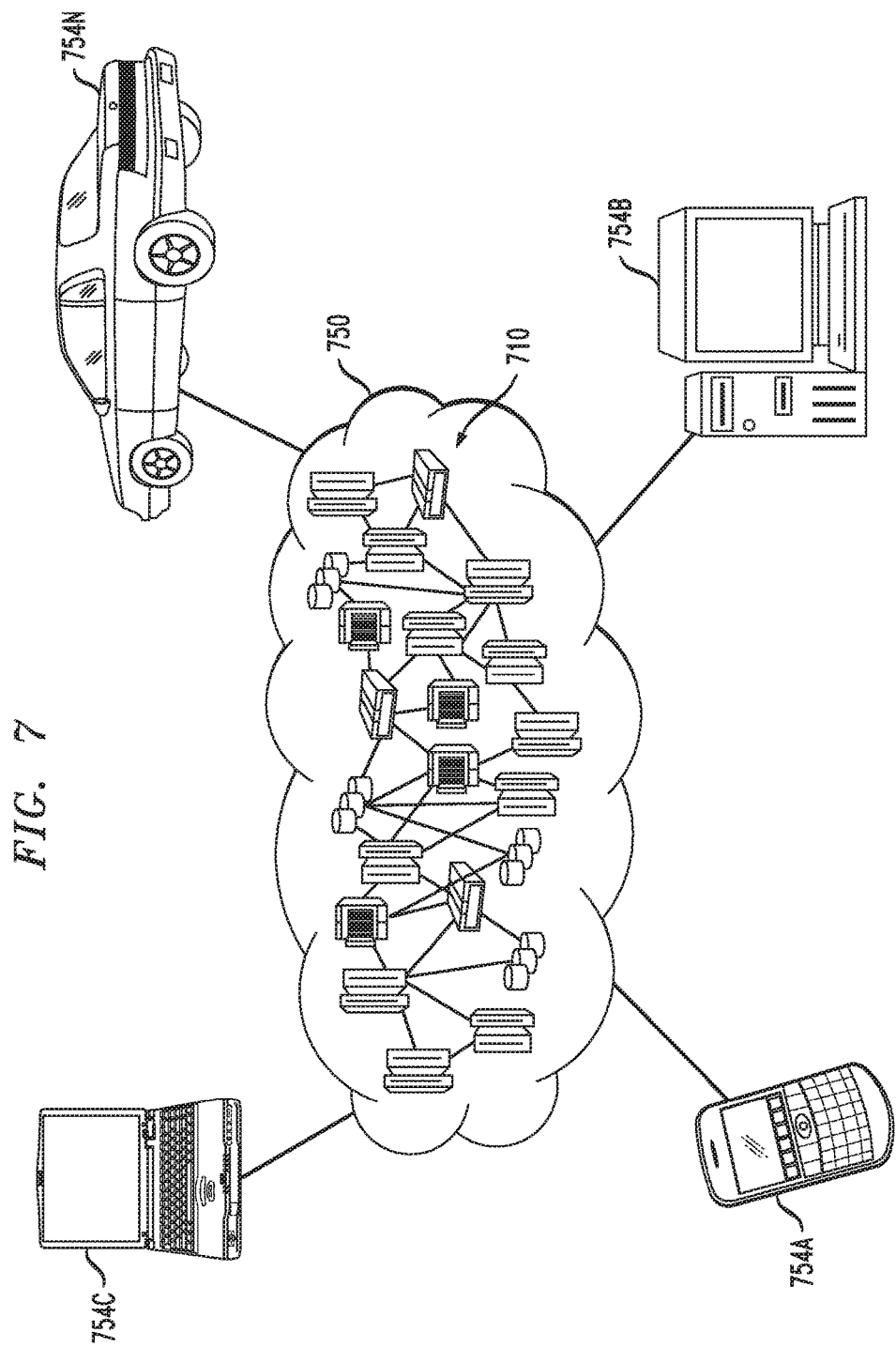
FIG. 7 depicts a cloud computing environment, according to an exemplary embodiment of the present invention.

Referring now to FIG. 7, illustrative cloud computing environment 750 is depicted. As shown, cloud computing environment 750 comprises one or more cloud computing nodes 710 with which local computing devices used by cloud consumers, such as, for example, a wearable device (not explicitly shown), a personal digital assistant (PDA) or cellular telephone 754A, desktop computer 754B, laptop computer 754C, and/or automobile computer system 754N may communicate. Nodes 710 may communicate with one another. They may be grouped (not shown) physically or virtually, in one or more networks, such as Private, Community, Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 7 are intended to be illustrative only and that computing nodes 710 and cloud computing environment 750 can communicate with any type of computerized device over any type of network and/or network addressable connection (e.g., using a web browser).

Figure 8:
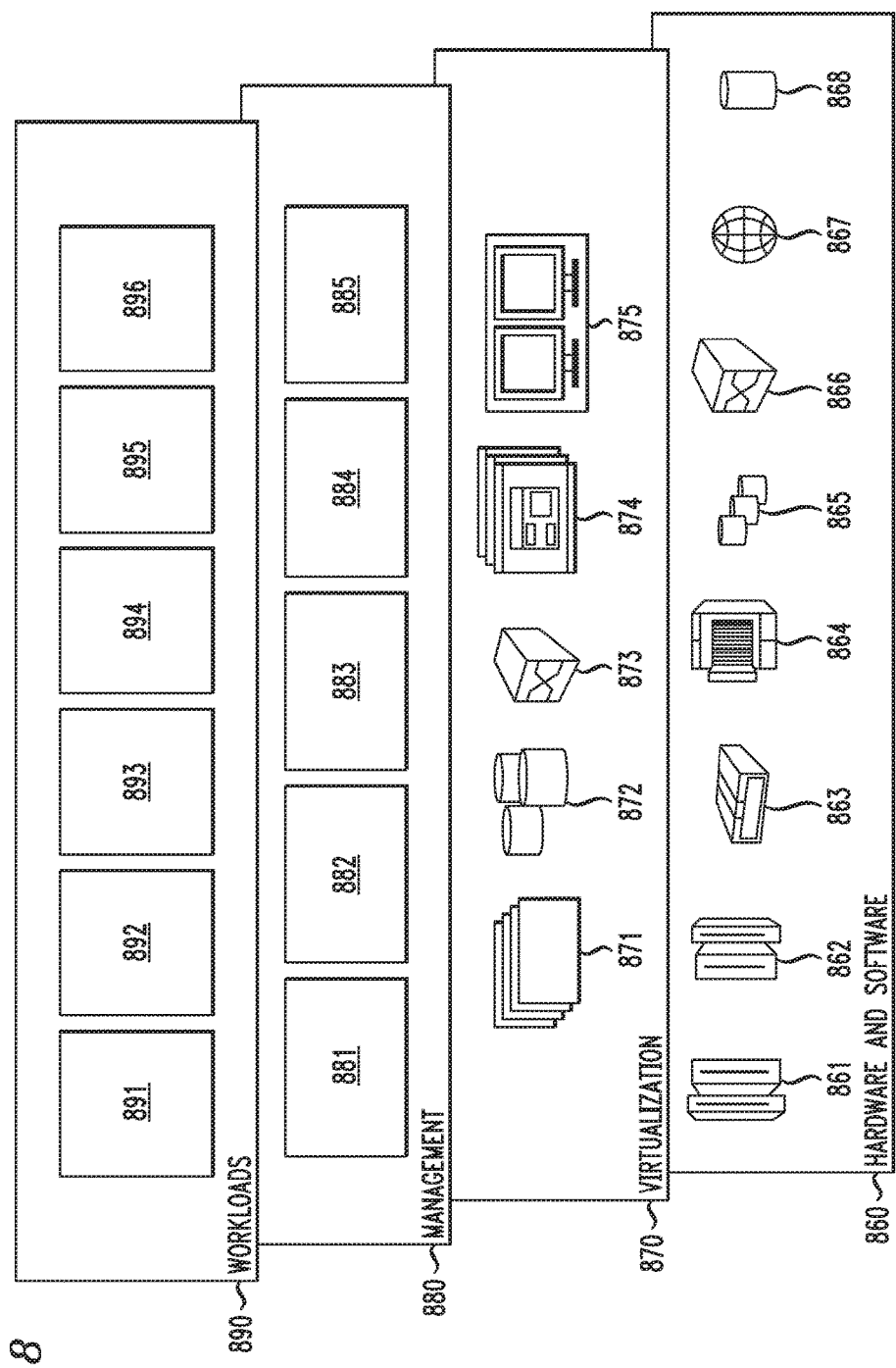
FIG. 8 depicts abstraction model layers, according to an exemplary embodiment of the invention.

Referring now to FIG. 8, a set of functional abstraction layers provided by cloud computing environment 750 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes 861; RISC (Reduced Instruction Set Computer) architecture based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities may be provided: virtual servers 871; virtual storage 872; virtual networks 873, including virtual private networks; virtual applications and operating systems 874; and virtual clients 875.

In one example, management layer 880 may provide the functions described below. Resource provisioning 881 provides dynamic procurement of computing resources and other resources that are utilized to perform tasks within the cloud computing environment. Metering and Pricing 882 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 883 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment may be utilized. Examples of workloads and functions which may be provided from this layer include: mapping and navigation 891; software development and lifecycle management 892; virtual classroom education delivery 893; data analytics processing 894; transaction processing 895; and lesion analysis and disease probability determination 896, which may implement the functionality described above with respect to FIGS. 1-7.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for image analysis, comprising:
receiving one or more current images of a lesion from a body of a person, wherein the one or more current images are electronically captured by and transmitted from a capture device;
analyzing the one or more current images of the lesion, wherein the analyzing comprises:
performing image processing to compare the one or more current images of the lesion captured at a first time to one or more previous images of the lesion captured at a second time prior to the first time; and
determining at least one difference between the one or more current images and the one or more previous images of the lesion based on the comparing;
determining a probability that the lesion will become diseased based on the analysis; and recommending at least one of a time for a future image capture of the lesion and a consultation with a practitioner based on the determined probability;
wherein the comparing is performed using a plurality of machine learning based engines;
wherein a first machine learning based engine of the plurality of machine learning based engines processes an arithmetical difference between the one or more current images and the one or more previous images of the lesion;
wherein a second machine learning based engine of the plurality of machine learning based engines processes a qualitative difference between the one or more current images and the one or more previous images of the lesion;
wherein a third machine learning based engine of the plurality of machine learning based engines processes the outputs of first and second machine learning based engines to yield a combined result; and
wherein the method is performed by at least one computer system comprising at least one memory and at least one processor coupled to the memory.

2. The method according to claim 1, further comprising training at least one of the plurality of machine learning based engines using lesion images each having a known label.

3. The method according to claim 1, wherein at least one of the plurality of machine learning based engines comprises a convolutional neural network (CNN).

4. The method according to claim 3, further comprising considering an output of the CNN for a pair of consecutive lesion images as an observed variable for a statistical model.

5. The method according to claim 1, further comprising analyzing metadata of the person, wherein the analyzing of the metadata comprises:
comparing current metadata corresponding to a later time to previous metadata corresponding to an earlier time than the later time; and
determining at least one difference between the current metadata and the previous metadata based on the comparing;
wherein the determining of the probability that the lesion will become diseased is further based on the analysis of the metadata.

6. The method according to claim 1, further comprising generating an approximation of the appearance of the lesion at any point in time between the first time and the second time.

7. The method according to claim 1, wherein performing the image processing comprises preprocessing the one or more current images and the one or more previous images of the lesion to have at least one of a same size, a same resolution and a same brightness.

8. The method according to claim 1, wherein performing the image processing comprises preprocessing the one or more current images and the one or more previous images of the lesion to be linearly aligned to each other.

9. The method according to claim 1, wherein determining the probability comprises:
building a time series of scores for probabilities that the lesion will become diseased; and
analyzing the time series of scores using a statistical model.

10. The method according to claim 1, wherein:
each of the plurality of machine learning based engines is trained with a different set of lesion images from each other, each lesion image having a known label.

11. The method according to claim 1, wherein recommending the time for the future image capture of the lesion comprises:
identifying a time when the probability that the lesion will become diseased exceeds a predefined threshold; and
assigning the identified time as the time for the future image capture of the lesion.

12. The method according to claim 1, wherein recommending the time for the future image capture of the lesion comprises:
defining upper and lower limits for the future image capture of the lesion according to different confidence thresholds for determining the probability that the lesion will become diseased.

13. The method according to claim 1, further comprising:
automatically transmitting the one or more current images to a device of a specialist if the probability that the lesion will become diseased exceeds a threshold.

14. A system for image analysis, comprising:
a memory and at least one processor coupled to the memory, wherein the at least one processor is configured to:
receive one or more current images of a lesion from a body of a person, wherein the one or more current images are electronically captured by and transmitted from a capture device;
analyze the one or more current images of the lesion, wherein in analyzing, the at least one processor is further configured to:
perform image processing to compare the one or more current images of the lesion captured at a first time to one or more previous images of the lesion captured at a second time prior to the first time; and
determine at least one difference between the one or more current images and the one or more previous images of the lesion based on the comparing;
determine a probability that the lesion will become diseased based on the analysis; and
recommend at least one of a time for a future image capture of the lesion and a consultation with a practitioner based on the determined probability;
wherein the comparing is performed using a plurality of machine learning based engines;
wherein a first machine learning based engine of the plurality of machine learning based engines processes an arithmetical difference between the one or more current images and the one or more previous images of the lesion;
wherein a second machine learning based engine of the plurality of machine learning based engines processes a qualitative difference between the one or more current images and the one or more previous images of the lesion; and
wherein a third machine learning based engine of the plurality of machine learning based engines processes the outputs of first and second machine learning based engines to yield a combined result.

15. The system according to claim 14, wherein in determining the probability, the at least one processor is further configured to:
build a time series of scores for probabilities that the lesion will become diseased; and
analyze the time series of scores using a statistical model.

16. The system according to claim 14, wherein:
each of the plurality of machine learning based engines is trained with a different set of lesion images from each other, each lesion image having a known label.

17. A computer program product for image analysis, the computer program product comprising a computer readable storage medium having program instructions embodied therewith, the program instructions executable by a processor to cause the processor to perform a method comprising:
receiving one or more current images of a lesion from a body of a person, wherein the one or more current images are electronically captured by and transmitted from a capture device;
analyzing the one or more current images of the lesion, wherein the analyzing comprises:
performing image processing to compare the one or more current images of the lesion captured at a first time to one or more previous images of the lesion captured at a second time prior to the first time; and
determining at least one difference between the one or more current images and the one or more previous images of the lesion based on the comparing;
determining a probability that the lesion will become diseased based on the analysis; and
recommending at least one of a time for a future image capture of the lesion and a consultation with a practitioner based on the determined probability;
wherein the comparing is performed using a plurality of machine learning based engines;
wherein a first machine learning based engine of the plurality of machine learning based engines processes an arithmetical difference between the one or more current images and the one or more previous images of the lesion;
wherein a second machine learning based engine of the plurality of machine learning based engines processes a qualitative difference between the one or more current images and the one or more previous images of the lesion; and
wherein a third machine learning based engine of the plurality of machine learning based engines processes the outputs of first and second machine learning based engines to yield a combined result.

* * * * *